US00PP34516P2

(12) United States Plant Patent
Schroll

(10) Patent No.: US PP34,516 P2
(45) Date of Patent: Aug. 23, 2022

(54) ***HYDRANGEA* PLANT NAMED 'SCHROLLA25'**

(50) Latin Name: *Hydrangea macrophylla*
Varietal Denomination: SCHROLLA25

(71) Applicant: Soren Schroll, Odense SV (DK)

(72) Inventor: Soren Schroll, Odense SV (DK)

(73) Assignee: SCHROLL MANAGEMENT ApS, Odense SV (DK)

( * ) Notice: Subject to any disclaimer, the term of this patent is extended or adjusted under 35 U.S.C. 154(b) by 0 days.

(21) Appl. No.: 17/701,489

(22) Filed: Mar. 22, 2022

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — C. Anne Whealy

(57) ABSTRACT

A new and distinct cultivar of *Hydrangea* plant named 'SCHROLLA25', characterized by its compact, upright and mounded plant habit; moderately vigorous growth habit and rapid growth rate; freely branching habit and strong and sturdy stems; dark green-colored leaves; mophead-type inflorescences with purplish pink-colored sterile flowers; when "blued", that is, treated with aluminum sulfate, sterile flowers are strong blue in color; long flowering period; and good postproduction quality and longevity as a container plant or cut flower and good garden performance.

3 Drawing Sheets

Figure 1:
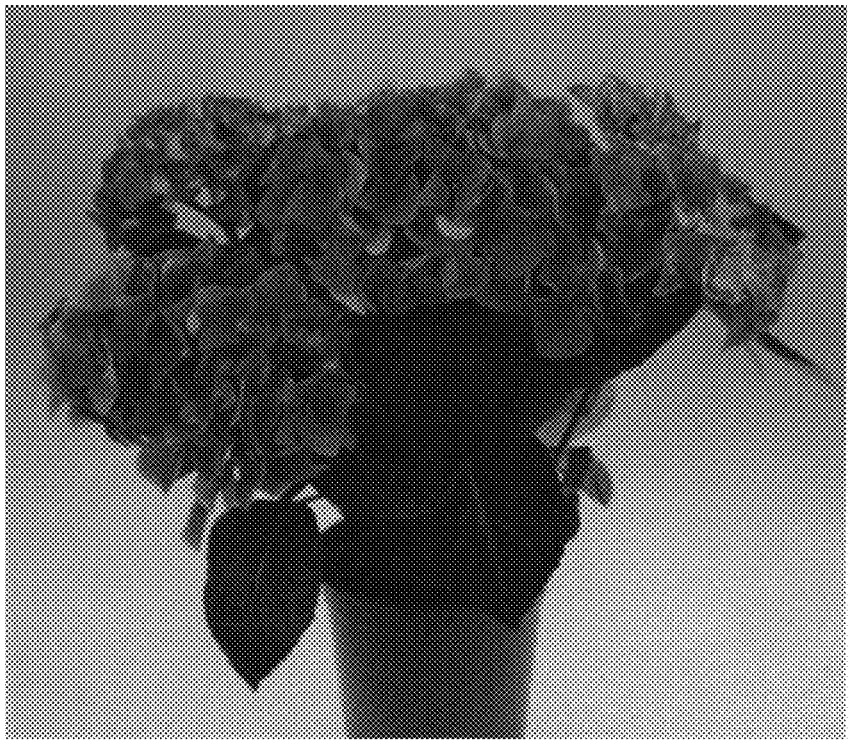

Botanical designation: *Hydrangea macrophylla.*
Cultivar denomination: 'SCHROLLA25'.

CROSS-REFERENCED TO A RELATED APPLICATION & STATEMENT REGARDING PRIOR DISCLOSURES BY INVENTOR/APPLICANT & ASSIGNEE

This application claims priority to a European Community Plant Breeders' Rights application filed on Sep. 7, 2021, application number 2021/2226. There have been no offers for sale anywhere in the world prior to the effective filing date of this Application and no accessibility to one of ordinary skill in the art could have been derived from the printed Plant Breeder's Rights documents.

The Inventor/Applicant and Assignee, Schroll Management ApS of Odense, Denmark assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla* and hereinafter referred to by the name 'SCHROLLA25'.

The new *Hydrangea* plant is a product of a planned breeding program conducted by the Inventor in Aarslev, Denmark. The objective of the breeding program was to develop new compact *Hydrangea* plants with strong stems, early flowering response and attractive leaf and flower coloration.

The new *Hydrangea* plant originated from a cross-pollination during the spring of 2013 of a proprietary selection of *Hydrangea macrophylla* identified as code number 32-00, not patented, as the female, or seed, parent with *Hydrangea macrophylla* 'Schrol1139-09-01a, disclosed in U.S. Plant Pat. No. 28,907, as the male, or pollen, parent. The new *Hydrangea* plant was discovered and selected by the Inventor during the spring of 2015 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2015 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLLA25'. These characteristics in combination distinguish 'SCHROLLA25' as anew and distinct *Hydrangea* plant:

1. Compact, upright and mounded plant habit.
2. Moderately vigorous growth habit and rapid growth rate.
3. Freely branching habit and strong and sturdy stems.

4. Dark green-colored leaves.
5. Mophead-type inflorescences with purplish pink-colored sterile flowers; when "blued", that is, treated with aluminum sulfate, sterile flowers are strong blue in color.
6. Long flowering period.
7. Good postproduction quality and longevity as a container plant or cut flower and good garden performance.

Plants of the new *Hydrangea* differ primarily from plants of the female selection parent in the following characteristics:

1. Plants of the new *Hydrangea* are more freely branching than plants of the female parent selection.
2. Plants of the new *Hydrangea* force faster than plants of the female parent selection.
3. When "blued", plants of the new *Hydrangea* and the female parent selection differ in sterile flower color as sterile flowers of plants of the new *Hydrangea* are strong blue in color whereas sterile flowers of plants of the female parent selection are clear blue in color.
4. Plants of the new *Hydrangea* tolerate cold storage better than plants of the female parent selection.

Plants of the new *Hydrangea* differ primarily from plants of the male parent, 'Schroll139-09-01a', in the following characteristics:

1. Plants of the new *Hydrangea* force faster than plants of 'Schroll139-09-01a'.
2. Sepal flower colors of plants of the new *Hydrangea*, whether "blued" or not, are more intense than the sepal flower colors of plants of 'Schroll139-09-01a'.
3. Inflorescences of plants of the new *Hydrangea* have longer postproduction longevity than inflorescences of plants of 'Schroll139-09-01a'.
4. Plants of the new *Hydrangea* tolerate cold storage better than plants of 'Schroll139-09-01a'.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the new *Hydrangea* are more compact than and not as vigorous as plants of 'H213901'.
2. Plants of the new *Hydrangea* have slightly smaller inflorescences than plants of 'H213901'.
3. Sepals of sterile flowers of the new *Hydrangea* are not as undulate as sepals of sterile flowers of 'H213901'.
4. Plants of the new *Hydrangea* and 'H213901' differ in sterile flower color, whether "blued" or not, as sterile flowers of plants of the new *Hydrangea* are lighter in color than sterile flowers of plants of 'H213901'.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the new *Hydrangea* are more vigorous than plants of 'H213906'.
2. Plants of the new *Hydrangea* force about two weeks faster than plants of 'H213906'.
3. Plants of the new *Hydrangea* and 'H213901' differ in sterile flower color, whether "blued" or not, as sterile flowers of plants of the new *Hydrangea* are brighter and lighter in color than sterile flowers of plants of 'H213901'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) comprises a side perspective view of a typical flowering plant of 'SCHROLLA25' grown in a container that has been "blued".

Figure 2:
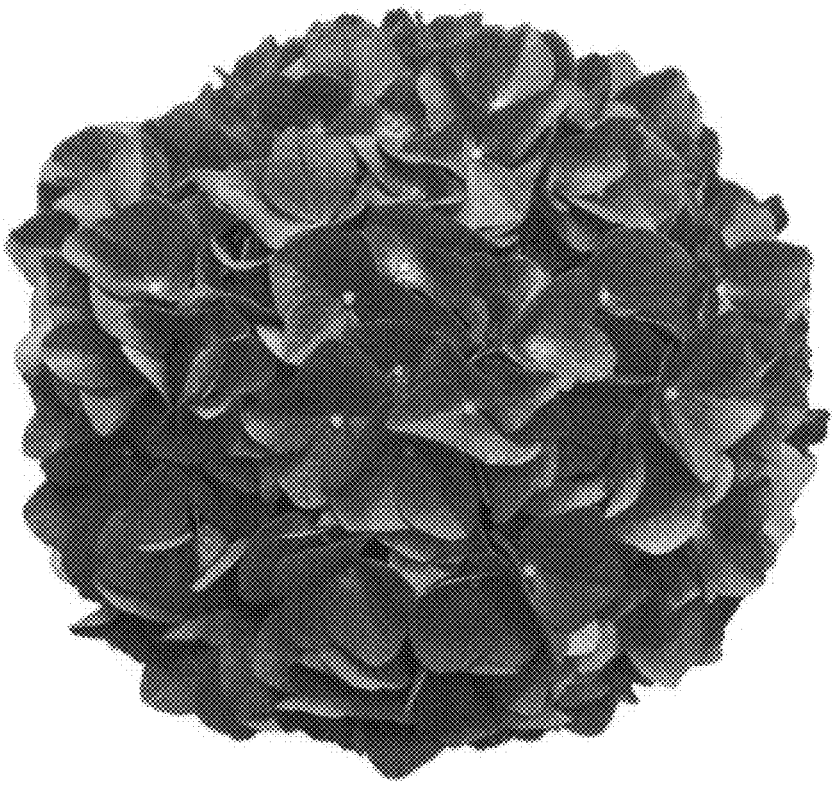

The photograph on the second sheet (FIG. 2) is a close-up view of a typical inflorescence of 'SCHROLLA25' that has been "blued".

Figure 3:
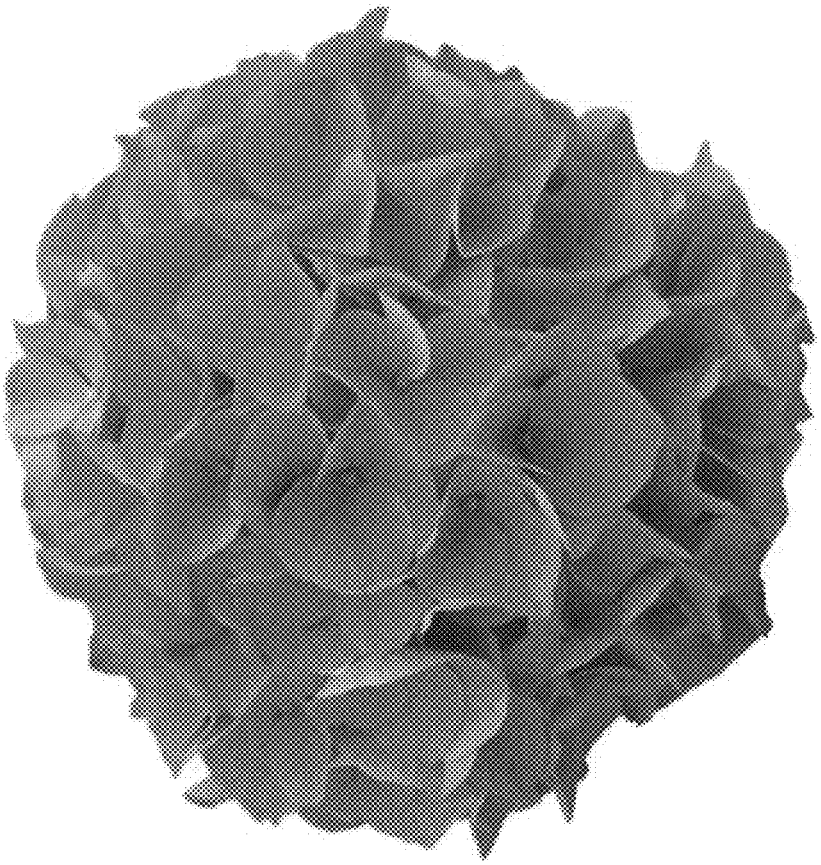

The photograph on the third sheet (FIG. 3) is a close-up view of a typical inflorescence of 'SCHROLLA25' that has not been "blued".

DETAILED BOTANICAL DESCRIPTION

Plants used in the aforementioned photographs and in the following description were grown during the summer in 13-cm containers in a glass-covered greenhouse in Aarslev, Denmark and under cultural practices typical of commercial *Hydrangea* production. Plants of the new *Hydrangea* were pinched two times and were one year old when the photographs and description were taken. During the production of the plants, day temperatures ranged from 15° C. to 25° C., night temperatures ranged from 15° C. to 20° C. and light levels ranged from 40 to 50 klux. In the following description, color references are made to The Royal Horticultural Society Colour Chart, 2007 Edition, except where general terms of ordinary dictionary significance are used.

Botanical description: *Hydrangea macrophylla* 'SCHROLLA25'.

Parentage:

*Female, or seed, parent.*—Proprietary selection of *Hydrangea macrophylla* identified as code number 32-00, not patented.

*Male, or pollen, parent.*—*Hydrangea macrophylla* 'Schroll139-09-01a', disclosed in U.S. Plant Pat. No. 28,907.

Propagation:

*Type cutting.*—By softwood cuttings.

*Time to initiate roots, summer.*—About 14 to 15 days at temperatures about 20° C.

*Time to initiate roots, winter.*—About 20 days at temperatures about 20° C.

*Time to produce a rooted young plant, summer.*—About four weeks at temperatures about 20° C. to 22° C.

*Time to produce a rooted young plant, winter.*—About five weeks at temperatures about 18° C. to 20° C.

*Root description.*—Medium in thickness, fibrous; typically close to N155D in color; actual color of the roots is dependent on substrate composition, water quality, fertilizer type and formulation, substrate temperature and physiological age of roots.

*Rooting habit.*—Freely branching; medium density.

Plant description:

*Plant and growth habit.*—Perennial sub shrub ; compact, upright and mounded plant habit; broadly inverted triangle; freely branching habit with about five to six lateral branches developing per plant; strong lateral branches; moderately vigorous growth habit and rapid growth rate.

*Plant height.*—About 25 cm to 30 cm.

*Plant diameter or area of spread.*—About 35 cm.

*Lateral branches.*—Length: About 25 cm to 27 cm. Diameter: About 5 mm to 7 mm. Internode length: About 3 cm to 4.5 cm. Strength: Strong, sturdy. Texture: Mostly smooth and glabrous, however, just below inflorescence, slightly pubescent. Color, developing: Close to N144C. Color, developed: Close to 144A. Lenticels: Density: High. Length: About 0.5 mm to 1 mm. Color: Close to N77A.

Leaf description:

*Arrangement.*—Opposite, decussate; simple.

*Length.*—About 7 cm to 9 cm.

*Width.*—About 5.5 cm to 7 cm.

*Shape.*—Ovate.

*Apex.*—Acute.

*Base.*—Attenuate.

*Margin.*—Serrate.

*Texture, upper surface.*—Smooth to rugose, glabrous.

*Texture, lower surface.*—Rugose, glabrous.

*Venation pattern.*—Pinnate, reticulate.

*Color.*—Developing leaves, upper surface: Close to 139A. Developing leaves, lower surface: Close to 139C. Fully expanded leaves, upper surface: Close to N138A; venation, close to 143D. Fully expanded leaves, lower surface: Close to N137D; venation, close to 144D.

*Petioles.*—Length: About 1.5 cm to 2 cm. Diameter: About 4 mm. Strength: Strong. Texture, upper and lower surfaces: Smooth, glabrous. Color, upper and lower surfaces: Close to 144D.

Inflorescence & flower description:

*Flower type and habit.*—Showy single sterile and inconspicuous single fertile flowers arranged on terminal mophead-type panicles; panicles globular in overall shape; sterile and fertile flowers face upright to outwardly depending on their position on the inflorescence; early flowering habit, plants begin flowering about ten to twelve weeks after forcing period.

*Natural flowering season.*—Long flowering period, continuous flowering during the mid to late summer in Northern Europe.

*Flower longevity, sterile flowers.*—Flowers last about four months on the plant and about three weeks as a cut flower; sterile flowers persistent.

*Flower longevity, fertile flowers.*—Flowers last about two weeks on the plant; fertile flowers not persistent.

*Quantity of flowers.*—Freely flowering habit with about 60 sterile flowers and about 25 fertile flowers per panicle.

*Fragrance.*—None detected.

*Panicle height.*—About 10 cm.

*Panicle diameter.*—About 15 cm to 17 cm.

*Flower diameter, sterile flowers.*—About 4 cm to 5.5 cm.

*Flower depth (height), sterile flowers.*—About 1.5 cm.

*Flower diameter, fertile flowers.*—About 4 mm.

*Flower depth (height), fertile flowers.*—About 4 mm.

*Flower shape, sterile flowers.*—Triangular to rounded, sepals facing upwardly.

*Flower shape, fertile flowers.*—Spherical.

*Flower buds, sterile flowers.*—Length: About 3 mm. Diameter: About 3 mm. Shape: Spherical. Color: Close to 144D.

*Flower buds, fertile flowers.*—Length: About 3 mm. Diameter: About 3 mm. Shape: Spherical. Color: Close to 145D.

*Petals, sterile flowers.*—Quantity and arrangement: Four, or occasionally three, in a single whorl. Length: About 2 mm. Width: About 1 mm. Shape: Ovate. Apex: Acute. Base: Obtuse. Margin: Entire. Texture, upper and lower surfaces: Smooth, glabrous. Color: When opening, upper and lower surfaces: Close to 150D. Fully opened, upper surface: Close to 62B; when "blued", close to 95B; becoming closer to 199D with subsequent development and when "blued", close to 98C. Fully opened, lower surface: Close to 62C; when "blued", close to 95B; becoming closer to 199D with subsequent development and when "blued", close to 98C.

*Petals, fertile flowers.*—Quantity and arrangement: Typically five in a single whorl. Length: About 3 mm. Width: About 2 mm. Shape: Oval. Apex: Acute. Base: Cuneate. Margin: Entire. Texture, upper and lower surfaces: Smooth, glabrous. Color: When opening and fully opened, upper surface: Close to 62D; when "blued", close to 101C; becoming closer to 165B with subsequent development. When opening and fully opened, lower surface: Close to 62D; when "blued", close to 100C; becoming closer to 165B to 165C with subsequent development.

*Sepals, sterile flowers.*—Quantity and arrangement: Four, or occasionally three, in a single whorl. Length: About 2 cm to 2.5 cm. Width: About 2.5 cm. Shape: Cordate. Apex: Broadly acute to obtuse. Base: Attenuate to cordate. Margin: Entire, undulate. Texture, upper surface: Smooth to rugose, glabrous. Texture, lower surface: Smooth to slightly ridged, glabrous. Color: When opening, upper and lower surfaces: Close to 150D. Fully opened, upper surface: Close to 63C; when "blued", close to 100B; with subsequent development, color becoming closer to 70D and when "blued", becoming closer to 101C with venation, close to 94C. Fully opened, lower surface: Close to 62B; when "blued", close to 100C; with subsequent development, color becoming closer to 69A and when "blued", becoming closer to 97B with venation, close to 96C.

*Sepals, fertile flowers.*—Quantity and arrangement: Five in a single whorl. Length: About 1 mm. Width: About 1 mm. Shape: Deltoid. Apex: Acute. Base: Cuneate. Margin: Entire. Texture, upper and lower surfaces: Slightly pubescent. Color: When opening and fully opened, upper surface: Proximally, close to 62D and distally, close to 145B; when "blued", proximally, close to 145D and distally, close to 145A. When opening and fully opened, lower surface: Proximally, close to 62D and distally, close to 145B; when "blued", proximally, close to 145D and distally, close to 145A.

*Pedicels, sterile flowers.*—Length: About 2.5 cm to 3 cm. Diameter: About 2 mm. Strength: Moderately strong. Aspect: Upright to about 135° from vertical. Texture: Pubescent. Color: Close to 62A.

*Pedicels, fertile flowers.*—Length: About 3 mm. Diameter: About 1 mm. Strength: Moderately strong. Aspect: Upright to about 90° from vertical. Texture: Pubescent. Color: Close to 64D; when "blued", close to 98B.

*Reproductive organs, sterile flowers.*—Stamens: Quantity per flower: About eight. Filament length: About 2 mm. Filament color: Close to 150D. Anther length: About 1 mm. Anther shape: Oval to reniform. Anther color: Close to 151D. Pollen amount: None observed. Pistils: Pistil quantity per flower: Two. Pistil length: About 2 mm. Stigma shape: Oval. Stigma color: Close to 155A. Style length: About 1 mm. Style color: Close to 155A. Ovary color: Close to 155D.

*Reproductive organs, fertile flowers.*—Stamens: Quantity per flower: Ten. Filament length: About 1 mm. Filament color: Close to 155D. Anther length: About 1 mm. Anther shape: Oval to reniform. Anther color: Close to 145B. Pollen amount: Scarce. Pollen color: Close to 158D. Pistils: Pistil quantity per flower: Three. Pistil length: About 3 mm. Stigma shape: Oval. Stigma color: Close to 155D. Style length: About 1 mm. Style color: Close to 155D.

*Seeds* (*present on fertile flowers only*).—Quantity per fertile flower: About 50. Length: About 0.5 mm. Diameter: About 0.1 mm. Color: Close to 164D.

Pathogen & pest resistance: To date, plants of the new *Hydrangea* have been observed to to tolerant to aphids and spider mites. Plants of the new *Hydrangea* have not been observed to be resistant to pathogens and other pests common to *Hydrangea* plants.

Garden performance: Plants of the new *Hydrangea* have been observed to tolerate wind, rain, full sunlight conditions and temperatures ranging from about 3° C. to 32° C.

It is claimed:

1. A new and distinct *Hydrangea* plant named 'SCHROLLA25' as illustrated and described.

* * * * *